United States Patent [19]

Higa

[11] Patent Number: 4,946,994

[45] Date of Patent: Aug. 7, 1990

[54] PREPARATION OF DITERTIARYBUTYLTELLURIDE

[75] Inventor: Kelvin T. Higa, Ridgecrest, Calif.

[73] Assignee: The United States of America as represented by the Secretary of the Navy, Washington, D.C.

[21] Appl. No.: 136,616

[22] Filed: Dec. 21, 1987

[51] Int. Cl.$^5$ ............................................. C07C 395/00
[52] U.S. Cl. ................................................... 562/899
[58] Field of Search ........................ 260/550; 562/899

[56] References Cited

U.S. PATENT DOCUMENTS 4,271,090 6/1981 Naglieri et al. ...................... 260/550

OTHER PUBLICATIONS

W. E. Hoke and P. J. Lemonias, "Low-Temperature Metalorganic Growth of CdTe and HgTe Films Using Ditertiarybutyltelluride", Applied Physics Letter, vol. 48, No. 24 (Jun. 16, 1986), pp. 1669–1671.

C. H. W. Jones and R. D. Sharma, "The Preparation of Di-t-Butyl Ditelluride and Di-t-Butyl Telluride and the $^{125}$Te NMR and Mössbauer Spectra of Some Dialkyl Tellurides and Ditellurides", Journal of Organometallic Chemistry, vol. 255, (1983), pp. 61–70.

S. Herberg et al., Z. Anorg. Allg. Chem., vol. 492, pp. 95–102 (1982).

S. Herberg et al., Chem. Abstracts, vol. 98, No. 88776q, (1983).

*Primary Examiner*—Mary E. Ceperley
*Attorney, Agent, or Firm*—Sol Sheinbein; Melvin J. Sliwka

[57] ABSTRACT

Ditertiarybutyltelluride and other symmetric dialkyltellurides are prepared from tellurium tetrachloride and metal alkyls in tetrahydrofuran. The reaction product is isolated by filtration followed by vacuum distillation.

24 Claims, No Drawings

PREPARATION OF DITERTIARYBUTYLTELLURIDE

BACKGROUND OF THE INVENTION

1. Field of the Invention

The present invention is related to the new preparation of ditertiarybutyltelluride.

2. Description of the Prior Art

Metal-Organic Chemical Vapor Deposition film growth of Mercury-Cadmium-Telluride ($Hg_{1-x}Cd_xTe$) is adversely affected by the high growth temperatures of 400° C. to 425° C. which are needed to crack diethyltelluride. At these temperatures, problems include mercury evaporation from the film and diffusion across the film-substrate interface.

Ditertiarybutyltelluride has been used to deposit films of HgTe and CdTe at temperatures as low as 250° C. with excellent results (W. E. Hoke and P. J. Lemonias, "Low-temperature metalorganic growth of CdTe and HgTe films using ditertiarybutyltelluride", Applied Physics Letter, vol. 48, no. 24 (Jun. 16, 1986), pp. 1669-1671). However, ditertiarybutyltelluride is in short supply since the presently used synthesis is a low yield process.

The existing process for preparing ditertiarybutyltelluride involves the reaction to tellurium tetrachloride with 2 equivalents of tertiarybutylmagnesium chloride and results in yields of less than 20% (C. H. W. Jones and R. D. Sharma, "THE PREPARATION OF DI-t-BUTYL DITELLURIDE AND DI-t-BUTYL TELLURIDE AND THE $^{125}$Te NMR AND MÖSSBAUER SPECTRA OF SOME DIALKYL TELLURIDES AND DITELLURIDES", Journal of Organometallic Chemistry, vol. 255, (1983) pp. 61-70).

SUMMARY OF INVENTION

Ditertiarybutyltelluride is one of the best tellurium source compounds for the low-temperature metalorganic chemical vapor deposition of epitaxial films of mercury-cadmium-telluride. The known method of preparing ditertiarybutyltelluride is an inefficient, low yield process. Ditertiarybutyltelluride can be prepared in high yield by the reaction of tellurium tetrachloride and tertiarybutyllithium in tetrahydrofuran. The final product is isolated via vacuum distillation.

An object of this invention is an efficient, high yield process for the preparation of ditertiarybutyltelluride as well as other dialkyltelluride compounds.

DETAILED DESCRIPTION OF THE INVENTION

According to the present invention, the composition of matter ditertiarybutyltelluride is prepared in an efficient process which is also useful for preparing other symmetrical dialkyltellurides.

Ditertiarybutyltelluride is prepared by a process in which tellurium tetrachloride in tetrahydrofuran and four equivalents of tertiarybutyllithium are allowed to react in an inert atmosphere between −78° C. and 25° C. The mixture is filtered, the solvent removed via distallation under inert gases and the final product isolated by vacuum distillation. Ditertiarybutyltelluride is produced in yields as high as 80%.

Other dialkyltellurides can be prepared by adding four equivalents of an alkyl metal to tellurium tetrachloride in a polar solvent between −78° C. and 25° C., where the alkyl group is a saturated or unsaturated hydrocarbon of the type methyl, ethyl, isopropyl or, tertiarybutyl. Alkyl metals such as alkyl sodium salts, alkyl potassium salts, or alkyllithium salts may be used, polar solvents such as dimethyl ether, diethyl ether, dimethoxyethane and tetrahydrofuran may be used. The reaction temperature is somewhat governed by the materials used. This temperature is about −45° C. for diethylether and −78° C. for tetrahydrofuran using the tertiarybutyllithium. The inert atmosphere may be the inert gases argon, helium or nitrogen. The pressure during vacuum distillation may be from 3 torr to 200 torr and temperatures between 25° C. to 110° C. The following example of the preparation of ditertiarybutyltelluride is given to illustrate but not limit the invention:

EXAMPLE

All operations were performed using standard Schlenk techniques under inert atmosphere and in the absence of light. A 1 liter Schlenk flask was charged with 20.2 grams of tellurium tetrachloride, $TeCl_4$, 100 mL of tetrahydrofuran, and a magnetic stirbar. The solution was cooled to −78° C. in a dry ice bath and a total of 187 mL of tertiarybutyllithium, whose concentration was 1.6 moles per liter in pentane, was added over a period of 30 minutes. After stirring for 1 hour at −78° C., the dry ice bath was removed and the mixture stirred at room temperature for another 2 hours. The solvent was removed via distillation under nitrogen and the product purified and isolated via vacuum distillation at 42°-43° C. at a pressure of 4 torr in 76% yield (13.7 grams). $^{125}$Te nuclear magnetic resonance spectrum of a 1 molar solution of the product in deuteriobenzene shows a single peak 103 downfield ppm of dimethyltelluride.

Modification and variation of the present invention are possible. It should be understood that, within the scope of the appended claims, the invention may be practiced otherwise than as specifically described.

What is claimed is:

1. The method of preparing dialkyltelluride compounds under an inert atmosphere in the absence of light, comprising the steps of:
   (a) adding at least four equivalents of an alkyl metal to one equivalent of tellurium tetrachloride in a solvent, said alkyl metal to be selected from the group consisting of alkyl sodium, alkyl lithium and alkyl potassium;
   (b) filtering a solid fraction from a liquid fraction thereof containing the liquid product;
   (c) distilling said liquid fraction under an inert gas, leaving a crude product; and
   (d) purifying a dialkyltelluride from said crude product by vacuum distillation.

2. The method of claim 1 wherein said alkyl is selected from the group consisting of methyl, ethyl, isopropyl and tertiarybutyl.

3. The method of claim 1 wherein said solvent is selected from the group consisting of tetrahydrofuran, dimethyl ether, diethyl ether and dimethoxyethane.

4. The method of claim 1 wherein said inert gas is selected from the group consisting of argon, nitrogen and helium.

5. The method of claim 1 wherein said purifying by vacuum distillation is at a pressure from about 3 torr to about 200 torr and a temperature from about 25° C. to about 110° C.

6. The method of preparing dialkyltelluride compounds under an inert atmosphere in the absence of light, comprising the steps of:
  (a) adding at least four equivalents of an alkyl metal to one equivalent of tellurium tetrachloride in a solvent while holding the temperature from about −78° C. to 25° C., said alkyl metal to be selected from the group consisting of alkyl sodium, alkyl lithium, and alkyl potassium;
  (b) filtering a solid fraction from a liquid fraction thereof containing the liquid product;
  (c) distilling said liquid fraction under an inert gas, leaving a crude product; and
  (d) purifying a dialkyltelluride from said crude product by vacuum distillation.

7. The method of claim 6 wherein said alkyl metal is added to tellurium tetrachloride over a period of about 30 minutes.

8. The method of claim 6 wherein said alkyl is selected from the group consisting of methyl, ethyl, isopropyl and tertiarybutyl.

9. The method of claim 6 wherein said solvent is selected from the group consisting of tetrahydrofuran, dimethyl ether, diethyl ether and dimethoxyethane.

10. The method of claim 6 wherein said inert gas is selected from the group consisting of argon, nitrogen and helium.

11. The method of claim 6 wherein said purifying by vacuum distillation is at a pressure of about 3 torr to about 200 torr and a temperature from about 25° C. to about 110° C.

12. The method of preparing dialkyltelluride compounds under an inert atmosphere in the absence of light, comprising the steps of:
  (a) adding at least four equivalents of an alkyl metal to one equivalent of tellurium tetrachloride in a solvent over a 30 minute time period while holding the temperature from about −78° C. to 25° C. in a dry-ice bath, said alkyl metal to be selected from the group consisting of alkyl sodium, alkyl lithium and alkyl potassium;
  (b) stirring the mixture for a first period of time while maintaining the dry-ice bath temperature;
  (c) removing the dry-ice bath;
  (d) stirring the mixture for a second period of time at room temperature;
  (e) filtering a solid fraction from a liquid fraction thereof containing the liquid product;
  (f) distilling said liquid fraction under an inert gas, leaving a crude product; and
  (g) purifying a dialkyltelluride from said crude product by vacuum distillation.

13. The method of claim 12 wherein said alkyl is selected from the group consisting of methyl, ethyl, isopropyl and tertiarybutyl.

14. The method of claim 12 wherein said solvent is selected from the group consisting of tetrahydrofuran, dimethyl ether, diethyl ether and dimethoxyethane.

15. The method of claim 12 wherein said first period of time for stirring is about 1 hour.

16. The method of claim 12 wherein said second period of time for stirring is about 2 hours.

17. The method of claim 12 wherein said inert gas is selected from the group consisting of argon, nitrogen and helium.

18. The method of claim 12 wherein said purifying by vacuum distillation is at a pressure of about 3 torr to 200 torr and a temperature from about 25° C. to about 110° C.

19. The method of preparing ditertiarybutyltelluride under inert atmosphere in the absence of light, comprising the steps of:
  (a) adding at least four equivalents of tertiarybutyl metal to one equivalent of tellurium tetrachloride in a solvent over a 30 minute time period while holding the temperature from about −78° C. to 25° C. in a dry-ice bath, said metal to be selected from the group consisting of sodium, lithium and potassium;
  (b) stirring the mixture for a first period of time while maintaining the dry-ice bath temperature;
  (c) removing the dry-ice bath;
  (d) stirring the mixture for a second period of time at room temperature;
  (e) filtering a solid fraction from a liquid fraction thereof containing the liquid product;
  (f) distilling said liquid fraction under an inert gas, leaving a crude product; and
  (g) purifying ditertiarybutyltelluride from said crude product by vacuum distillation.

20. The method of claim 19 wherein said solvent is selected from the group consisting of tetrahydrofuran, dimethyl ether, diethyl ether and dimethoxyethane.

21. The method of claim 19 wherein said first time for stirring is about 1 hour.

22. The method of claim 19 wherein said second time for stirring, after removing the dry-ice bath, is about 2 hours.

23. The method of claim 19 wherein said inert gas is selected from the group consisting of argon, nitrogen and helium.

24. The method of claim 19 wherein said purifying by vacuum distillation is at a pressure of about 3 torr to about 200 torr and a temperature from about 25° C. to about 110° C.

* * * * *